U S 0 0 8 1 4 2 7 4 0 B 2

US008142740B2

(12) United States Patent
Self et al.

(10) Patent No.: US 8,142,740 B2
(45) Date of Patent: Mar. 27, 2012

(54) SAMPLE RACK SYSTEM

(75) Inventors: Brian Austin Self, Germantown, MD (US); James Hal Godsey, Potomac, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 0 days.

(21) Appl. No.: 12/617,485

(22) Filed: Nov. 12, 2009

(65) Prior Publication Data

US 2010/0203643 A1     Aug. 12, 2010

Related U.S. Application Data

(63) Continuation-in-part of application No. 12/588,304, filed on Oct. 9, 2009.

(60) Provisional application No. 61/242,671, filed on Sep. 15, 2009, provisional application No. 61/183,857, filed on Jun. 3, 2009, provisional application No. 61/113,855, filed on Nov. 12, 2008, provisional application No. 61/122,621, filed on Dec. 15, 2008, provisional application No. 61/185,081, filed on Jun. 8, 2009.

(51) Int. Cl.
*B01L 9/06* (2006.01)
*G01N 35/02* (2006.01)
*B65D 1/36* (2006.01)

(52) U.S. Cl. ........ 422/561; 206/139; 206/203; 206/483; 206/564; 422/65; 422/560; 422/562; 422/566; 435/809; 436/43; 436/47; 436/809

(58) Field of Classification Search .................. 206/139, 206/153, 160, 174, 203, 427, 483, 590, 564; 211/74, 126.1; 422/65, 104, 942, 948, 560–562, 422/566; 435/288.4, 809; 436/43, 47, 809
See application file for complete search history.

(56) References Cited

U.S. PATENT DOCUMENTS

| 2,360,978 | A | * | 10/1944 | Putter | 211/74 |
|---|---|---|---|---|---|
| 2,979,210 | A | * | 4/1961 | Patterson | 211/74 |
| 3,375,934 | A | * | 4/1968 | Bates | 211/72 |
| 3,379,315 | A | * | 4/1968 | Broadwin | 211/72 |
| 3,491,894 | A | * | 1/1970 | Brown | 211/74 |
| 3,744,665 | A | | 7/1973 | Spoto | |
| 3,905,482 | A | * | 9/1975 | Knulst | 211/74 |
| 3,918,920 | A | * | 11/1975 | Barber | 422/104 |
| 4,039,286 | A | * | 8/1977 | Keller et al. | 436/47 |
| 4,096,965 | A | * | 6/1978 | Lessnig et al. | 220/523 |
| 4,124,122 | A | * | 11/1978 | Emmitt | 211/74 |
| 4,368,913 | A | * | 1/1983 | Brockmann et al. | 294/106 |
| 4,482,522 | A | * | 11/1984 | Baudisch et al. | 422/104 |
| 4,534,465 | A | * | 8/1985 | Rothermel et al. | 206/443 |
| 4,544,193 | A | * | 10/1985 | Dunn et al. | 294/86.4 |

(Continued)

FOREIGN PATENT DOCUMENTS

WO     WO 2007/048042     4/2007

*Primary Examiner* — Arlen Soderquist
(74) *Attorney, Agent, or Firm* — Hunton & Williams

(57) ABSTRACT

A rack for an automated processing system. The rack includes a number of wells adapted to hold at least a first sample container having a first size, and a second sample container having a second size. The second size, which may be a diameter, a height, or both, is substantially different from the first size. A structure joins the wells. The rack is adapted to fit in an automated processing system that is adapted to remove both the first sample container and the second sample container from the rack.

22 Claims, 4 Drawing Sheets

U.S. PATENT DOCUMENTS

| | | | | |
|---|---|---|---|---|
| 4,545,723 A | * | 10/1985 | Clark | 414/730 |
| 4,632,631 A | * | 12/1986 | Dunlap | 414/736 |
| 4,692,308 A | * | 9/1987 | Riley et al. | 422/65 |
| 4,740,025 A | * | 4/1988 | Nelson | 294/99.1 |
| 4,798,095 A | * | 1/1989 | Itoh | 73/863.01 |
| 4,805,772 A | * | 2/1989 | Shaw et al. | 206/443 |
| 4,938,369 A | * | 7/1990 | Carilli | 211/74 |
| 4,968,077 A | * | 11/1990 | Redmon et al. | 294/16 |
| 4,974,460 A | * | 12/1990 | Baxter | 73/864.91 |
| 5,080,232 A | * | 1/1992 | Leoncavallo et al. | 206/446 |
| 5,116,578 A | * | 5/1992 | Baxter | 422/63 |
| 5,137,693 A | * | 8/1992 | Mawhirt | 422/104 |
| 5,202,262 A | | 4/1993 | Lemonnier | |
| 5,397,542 A | * | 3/1995 | Nelms et al. | 422/104 |
| 5,417,922 A | * | 5/1995 | Markin et al. | 422/65 |
| 5,456,887 A | * | 10/1995 | Calvo et al. | 422/104 |
| 5,472,669 A | * | 12/1995 | Miki et al. | 422/63 |
| 5,479,969 A | * | 1/1996 | Hardie et al. | 141/130 |
| 5,491,067 A | * | 2/1996 | Setcavage et al. | 435/7.25 |
| 5,525,298 A | * | 6/1996 | Anami | 422/63 |
| 5,536,056 A | * | 7/1996 | Clarke et al. | 294/119.3 |
| 5,551,828 A | * | 9/1996 | Iles | 414/757 |
| 5,579,929 A | * | 12/1996 | Schwartz | 211/74 |
| 5,589,137 A | * | 12/1996 | Markin et al. | 422/104 |
| 5,651,941 A | * | 7/1997 | Stark et al. | 422/104 |
| 5,658,532 A | * | 8/1997 | Kurosaki et al. | 422/64 |
| 5,687,849 A | * | 11/1997 | Borenstein et al. | 206/446 |
| 5,700,429 A | * | 12/1997 | Buhler et al. | 422/104 |
| 5,721,384 A | * | 2/1998 | Tanihata | 73/864.81 |
| 5,775,755 A | * | 7/1998 | Covert et al. | 294/88 |
| 5,851,042 A | * | 12/1998 | Bankuty et al. | 294/106 |
| 5,872,361 A | | 2/1999 | Paoli et al. | |
| 5,928,952 A | * | 7/1999 | Hutchins et al. | 436/50 |
| 5,985,219 A | * | 11/1999 | Lind | 422/104 |
| 5,996,818 A | * | 12/1999 | Boje et al. | 211/74 |
| 6,060,022 A | * | 5/2000 | Pang et al. | 422/65 |
| 6,111,238 A | * | 8/2000 | Fix et al. | 219/700 |
| 6,123,205 A | * | 9/2000 | Dumitrescu et al. | 211/74 |
| 6,156,275 A | * | 12/2000 | Dumitrescu et al. | 422/104 |
| 6,161,759 A | * | 12/2000 | Moss et al. | 235/462.01 |
| 6,203,760 B1 | * | 3/2001 | van der Plaats et al. | 422/63 |
| 6,227,053 B1 | * | 5/2001 | Purpura et al. | 73/627 |
| 6,257,091 B1 | * | 7/2001 | Cohen et al. | 81/3.2 |
| 6,274,092 B1 | * | 8/2001 | Itoh | 422/104 |
| 6,293,750 B1 | * | 9/2001 | Cohen et al. | 414/744.4 |
| 6,426,228 B1 | * | 7/2002 | Cohen et al. | 436/47 |
| 6,435,582 B1 | * | 8/2002 | DaSilva et al. | 294/94 |
| 6,444,472 B1 | | 9/2002 | Cohen et al. | |
| 6,458,324 B1 | * | 10/2002 | Schinzel | 422/65 |
| 6,598,474 B2 | * | 7/2003 | Purpura et al. | 73/290 V |
| 6,599,476 B1 | * | 7/2003 | Watson et al. | 422/63 |
| 6,620,585 B1 | | 9/2003 | Zyskind | |
| 6,843,357 B2 | * | 1/2005 | Bybee et al. | 198/345.3 |
| 6,887,432 B2 | * | 5/2005 | Kansy et al. | 422/102 |
| 6,919,044 B1 | * | 7/2005 | Shibata et al. | 422/63 |
| 6,932,942 B2 | * | 8/2005 | Itoh | 422/104 |
| 7,000,785 B2 | | 2/2006 | Jafari et al. | |
| 7,118,892 B2 | | 10/2006 | Ammann et al. | |
| 7,152,736 B1 | * | 12/2006 | Menichini | 206/443 |
| 7,287,792 B2 | * | 10/2007 | Tye | 294/103.1 |
| 7,435,387 B2 | * | 10/2008 | Itoh | 422/99 |
| 7,610,115 B2 | * | 10/2009 | Rob et al. | 700/245 |
| 2002/0086431 A1 | | 7/2002 | Markham et al. | |
| 2002/0090320 A1 | | 7/2002 | Burow et al. | |
| 2002/0125230 A1 | | 9/2002 | Haight et al. | |
| 2002/0186363 A1 | | 12/2002 | Samsoondar et al. | |
| 2003/0069699 A1 | | 4/2003 | Ekins et al. | |
| 2004/0029135 A1 | | 2/2004 | Ramberg | |
| 2004/0076546 A1 | | 4/2004 | Bissett | |
| 2004/0209374 A1 | | 10/2004 | Kopf-Sill et al. | |
| 2005/0069913 A1 | | 3/2005 | Mian et al. | |
| 2006/0136095 A1 | | 6/2006 | Rob et al. | |
| 2008/0160539 A1 | | 7/2008 | Murphy et al. | |
| 2008/0247914 A1 | | 10/2008 | Edens et al. | |
| 2009/0098022 A1 | | 4/2009 | Tokhtuev et al. | |
| 2010/0105060 A1 | | 4/2010 | Eder et al. | |
| 2010/0159463 A1 | | 6/2010 | Eder et al. | |

* cited by examiner

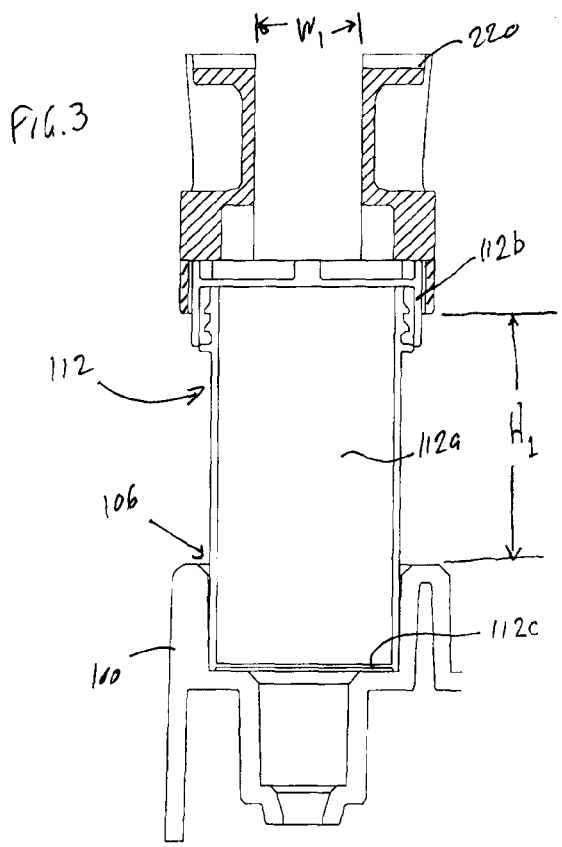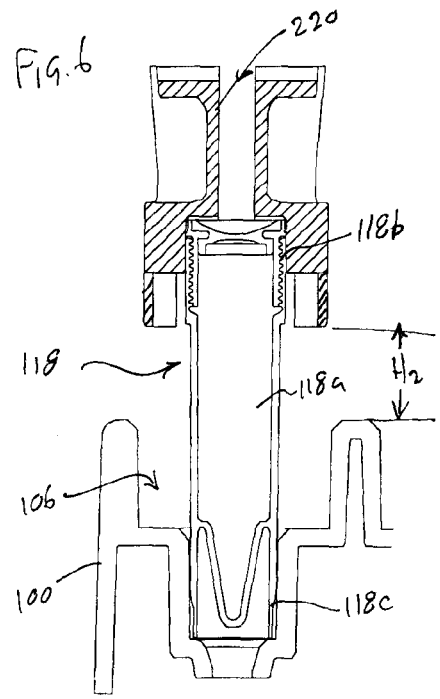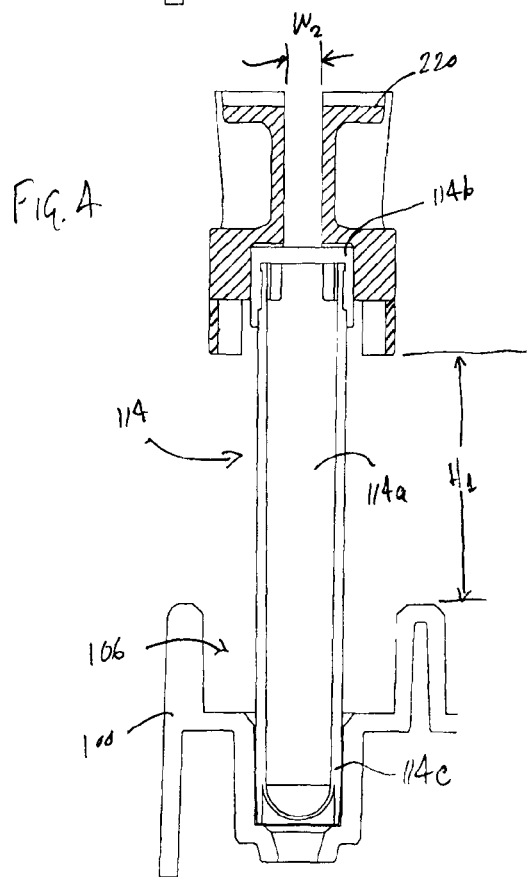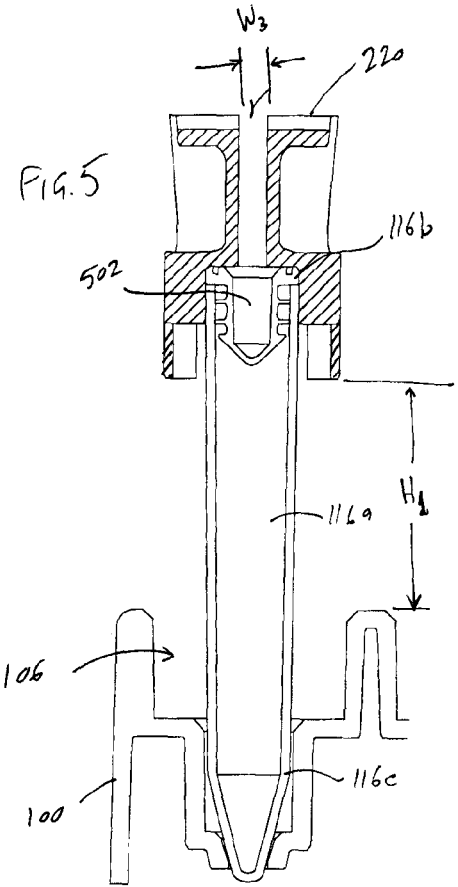

SAMPLE RACK SYSTEM

CROSS-REFERENCE TO RELATED APPLICATIONS

This application is a continuation-in-part and claims priority to U.S. patent application Ser. No. 12/588,304 filed Oct. 9, 2009, and claims the benefit of U.S. Provisional Patent Application Ser. Nos. 61/242,671 Sep. 15, 2009; 61/183,857 filed Jun. 3, 2009; 61/113,855 filed Nov. 12, 2008; 61/122,621 filed Dec. 15, 2008; and 61/185,081 filed Jun. 8, 2009. The present application incorporates herein by reference each of the foregoing references.

BACKGROUND

1. Field of the Art

The present disclosure relates to automated sample processing systems, and in particular to rack and sample handling systems that may provide greater flexibility and utility in automated processing systems.

2. Description of Related Art

It is well-known that physicians and other care-givers often take biological samples from patients, and place those samples in a sample container, such as a test tube or a vial. Given the cost, inconvenience and special skills necessary to actually test the sample, caregivers often send samples to an on-site or off-site laboratory ("lab") that will process and test the sample, then return the test results to the caregiver. To facilitate the testing process, the caregivers often use uniform sample containers for each type of test. For example, blood samples, urine samples, and tissue or cytology/molecular samples each may be stored in a unique type of container. The need to use of different containers for different kinds of sample may be dictated by various factors, such as sample volume, but in any event it has the added benefit that it is easier to tell different sample types apart, and therefore is more difficult to accidentally test one kind of sample in a process intended for another type of sample.

In some cases, a testing lab may require caregivers to use particular sample containers so that the lab does not have to accommodate multiple container types in its handling and testing equipment. This is particularly true where the lab relies on automated systems to help process the samples.

Furthermore, a medical company that develops a unique test protocol may provide caregivers with unique containers to hold test samples intended to be tested using that protocol. Such containers may contain a liquid medium in which the sample is stored. Examples of such protocols include the "Hybrid Capture 2" and "Next Generation Hybrid Capture®️ High Risk" assays developed by QIAGEN Gaithersburg, Inc. of Gaithersburg, Md. ("Qiagen"). These protocols may accommodate specimens in a medium, such as the PreservCyt®️ ("PC") medium (also from Qiagen). A company providing multiple test protocols may provide unique containers for each protocol to ensure that samples intended for each protocol can be distinguished from one another and the proper test is performed on each sample. This is particularly true where the protocols are used to test for the same condition, as protocols may require substantially different processing steps even though they both detect the same condition.

Given the common use of different containers for different sample types and testing protocols, companies producing testing equipment (which may or may not be the companies producing the protocols and/or containers) typically configure the equipment to hold and process samples contained in the particular container used to hold the sample. This equipment can range from simple sample racks used to hold samples during manual testing, to racks, grippers and other devices used in automated sample-processing systems. In many cases, an automated sample processing machine may be constructed such that it handles only one kind of biological sample container, which helps to ensure that the equipment can not be used to perform a test on the wrong kind of sample.

SUMMARY

In one aspect, there is provided a rack for an automated processing system. The rack includes a number of wells that each are adapted to alternatively hold at least a first sample container having a first size, and a second sample container having a second size. The second size is substantially different from the first size. The rack also includes a structure joining the plurality of wells to form a rack. The rack is adapted to fit in an automated processing system that is adapted to remove both the first sample container and the second sample container from the rack.

In another aspect, there is provided an automated sample processing system having a first sample container, a second sample container, a rack, and a processing machine. The second sample container has at least one dimension that is substantially different from at least one corresponding dimension of the first sample container. The rack has a number of wells, each of which is configured to alternately hold the first sample container and second sample container, and a structure joining the wells. The processing machine can receive the rack, and has a gripper having one or more movable grips adapted to alternately grasp the first sample container and the second sample container to permit the gripper to remove the first sample container and the second sample container from the rack.

In another aspect, there is provided a rack and sample container system having a first sample container having a first height, a second sample container having at second height, a third sample container having a third height, and a rack having a number of wells. Each well has a first well shape adapted to hold the first sample container with an upper end of the first sample container at a first predetermined distance from the rack, a second well shape adapted to hold the second sample container with an upper end of the second sample container at a second predetermined distance from the rack, and a third well shape adapted to hold the third sample container with an upper end of the third sample container at a third predetermined distance from the rack.

In another aspect, there is provided a method for picking sample containers from a sample rack. The method includes positioning a gripper at a first height above a sample well on a sample rack, moving at least two grip fingers towards one another along a substantially horizontal path, each grip finger having a first grip member and a second grip member, each second grip member being located above each first grip member and the second grip members being located on the fingers such that the second grip members are closer to one another than the first grip members, and engaging a sample located along the path, the sample being any of a group of samples having different diameters and vertical heights relative to one another.

BRIEF DESCRIPTION OF THE DRAWINGS

FIG. 3 is a cutaway elevation view of a portion of the sample rack and gripper of FIG. 2, shown with a first exemplary sample vial.

FIG. 4 is a cutaway elevation view of a portion of the sample rack and gripper of FIG. 2, shown with a second exemplary sample vial.

FIG. 5 is a cutaway elevation view of a portion of the sample rack and gripper of FIG. 2, shown with a third exemplary sample vial.

FIG. 6 is a cutaway elevation view of a portion of the sample rack and gripper of FIG. 2, shown with a fourth exemplary sample vial.

DETAILED DESCRIPTION

The present disclosure provides exemplary embodiments of sample racks and grippers that may be used together or separately to permit a single machine to process samples provided in different kinds of containers. As noted above, different kinds of biological samples typically are provided in different kinds of sample containers, and there is a strong incentive to keep such samples separate from one another to avoid confusion and improper processing. Thus, it appears that processing equipment may be made such that it can process only a single kind of sample. While machines such as the one shown in U.S. Patent Publication No. 2008/0247914 (which is incorporated herein by reference) may be equipped with alternative holding racks to hold control samples that are different from the patient samples, the control samples are not mixed with patient samples on a single rack, and the patient sample rack appears to have no structure adapted to accommodate multiple different sample containers. It has been found, however, that embodiments of the invention can permit the safe handling of various different sample containers and sample types in a single rack or by a single gripping device.

Figure 1:
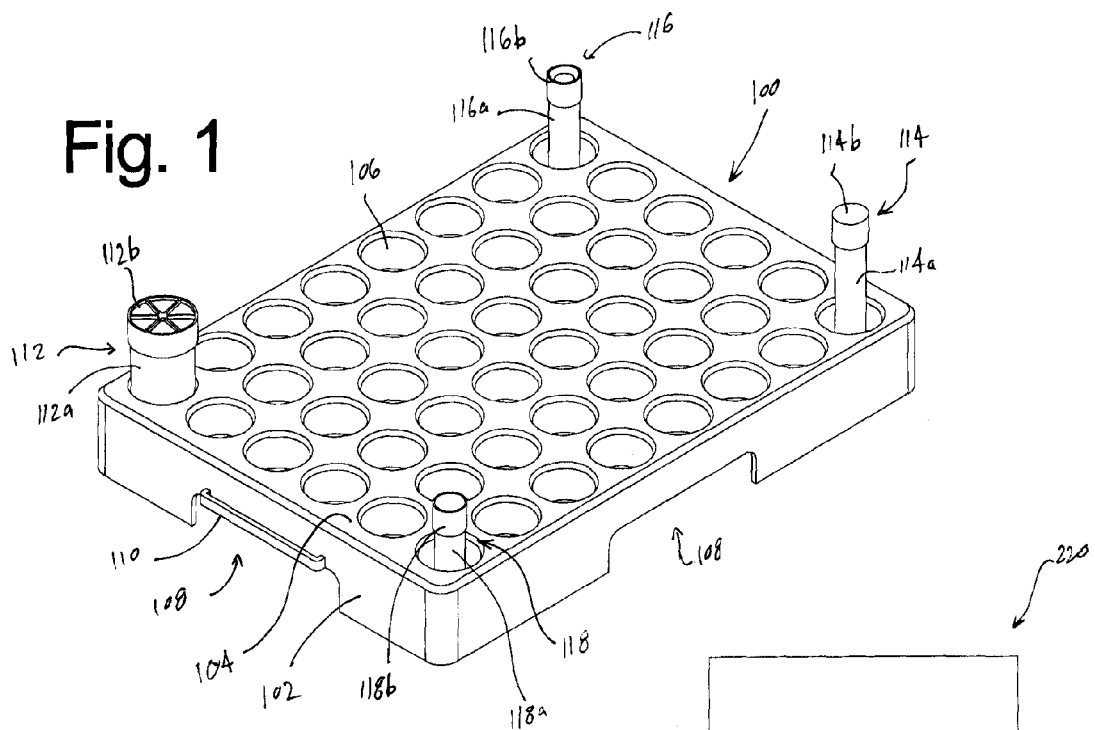
FIG. 1 is an isometric view of a sample rack according to one exemplary embodiment of the invention, shown with various sample vials held in the rack.

FIG. 1 illustrates and exemplary embodiment of a sample rack 100 according to one aspect of the invention. The rack 100 generally comprises a rectangular structure having a perimeter wall 102, and upper surface 104, and a plurality of sample wells 106 extending downward from the upper surface 104. The rack 100 may include cutouts 108 or other handles or grippable portions, which may help a user lift and move the rack 100. If desired, the rack 100 also may include one or more ledges 110 or other features that are adapted to be used by a conveyor system within a machine to move the rack 100. Any number of variations on the basic rack structure may be made. For example, the rack 100 may shaped differently (e.g., semicircular, triangular, etc.), the wells 106 may protrude from a lower wall or may be linked together to form the rack 100 using any other suitable structure, or other changes may be made, as necessary or desired. In addition, while the shown rack 100 may be readily formed by injection molding techniques, other manufacturing methods may be used as desired.

It is expected that the rack 100 will have the greatest utility if it is configured to be handled both by a human user and by a processing machine. However, embodiments may be adapted solely for human use or machine use. For example, another embodiment of a rack according to the invention may comprise a rack that is installed as a fixture in a processing machine, and is not removable or at least is not removable under normal operating conditions. Still another embodiment may be a rack that is adapted for human manipulation, but does not have any special features designed to facilitate use in a particular machine.

As shown in FIG. 1, the rack 100 is adapted to hold a number of different kinds of sample vials 112, 114, 116, 118. As shown, these vials may have different lengths, shapes, or diameters, and may have different sizes and kinds of caps. For example a first vial 112, which is shown in more detail in FIG. 3, may comprise a relatively large-diameter cylindrical vessel body 112a having a threaded cap 112b and a squared bottom 112c (as used herein "squared bottom" means the lower end of the vial has a shape that would rest on a surface perpendicular to the vial axis and support the vial upright without additional support). The second vial 114, shown in more detail in FIG. 4, may comprise a smaller-diameter, but relatively tall body 114a having a twist-on (e.g., bayonet-fitting or threaded) cap 114b, and a squared bottom 114c. In this embodiment, the squared bottom 114c has a rounded wall that is surrounded by a skirt that provides the squared feature. The third vial 116, shown in more detail in FIG. 5, may comprise a smaller-diameter, and even taller, body 116a having a push-cap 116b, and a contoured bottom 116c ("contoured bottom" means the vial lacks a structure that will support the vial upright without additional support). The fourth vial 118, shown in more detail in FIG. 6, may comprise a relatively short, smaller-diameter body 118a having a threaded cap 118b, and a squared bottom 118c. Of course, these sample vials are intended to be exemplary, and other shapes, sizes and combinations of shapes and sizes may be used in other embodiments.

Referring to FIGS. 2-6, the sample rack 100 may be configured to accommodate a number of different vials by using a variety of well shapes to accommodate each vial shape.

Figure 2:
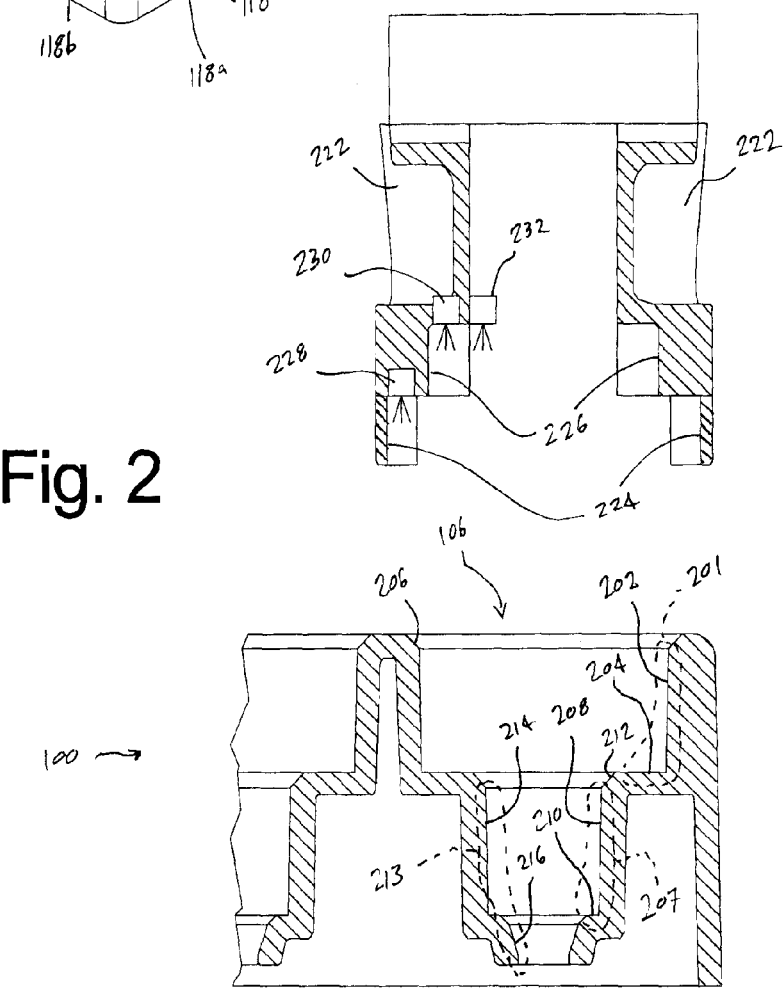
FIG. 2 is a cutaway elevation view of a portion of the sample rack of FIG. 1 and a gripper according to one exemplary embodiment of the invention.

As shown in FIGS. 2 and 3, the first well shape 201 comprises a combination of a first lateral support that retains the bottom of the first vial 112 in the lateral direction and a first vertical support that supports the first vial 112 in the vertical direction. The exemplary first lateral support is shown in the shape of a first cylindrical wall 202 and the exemplary first vertical support is shown in the shape of a first radial wall 204 extending inwardly from the bottom of the first cylindrical wall 202. While the first cylindrical wall 202 and first radial wall 204 are joined, this is not required, and they may be spaced apart or separated by a gap (such as a fluid gutter to hold any spilled fluids). The first cylindrical wall 202 is approximately the same size as but slightly larger than the outer diameter of the bottom of the first vial 112, but a slight gap or interference fit may be provided as desired. The use of a gap or interference fit may be suggested by manufacturing tolerance variables, as known in the art, with greater variations in the size of the vial suggesting, but not mandating, a slightly larger cylindrical wall size. If necessary, some degree of flexure may be built into the cylindrical wall or the vial to help ensure consistent insertability and suitable holding of the first vial 112. To accommodate alignment, insertion and removal, the first cylindrical wall 202 may be tapered slightly to narrow towards the bottom. A chamfer 206 or rounded lip may be provided at the top of the first cylindrical wall 202 to facilitate insertion of the sample vials by increasing tolerance to misalignment. The first radial wall 204 extends radially inward from the first cylindrical wall 202, and may be horizontal, as shown, or angled upward or downward as desired. The first well shape 201 also may include flexible or highfriction grips (not shown), spring-loaded tabs or the like, to help accommodate size variations or help retain the first vial 112 in place.

It will be readily appreciated that the first cylindrical wall 202 and first radial wall 204 can include cutouts, voids, or shape variations that will not take them outside the scope of the terminology used to describe the general shape of the wall. For example, the first cylindrical wall 202 can be formed by a plurality of pins or ribs, rather than a solid wall, and still form, for purposes of the invention, a cylindrical wall. As another example, the first radial wall 204 may comprise one or more discrete projections that extend inward from the first cylindrical wall 202, rather than being a continuous surface. Thus, where terms like "cylindrical," "radial," "conical" and so on are used above and below to describe walls and other shapes, those terms encompass structures that specifically match the named shape, partial structures that match the named shape but include voids or variations from the named shape, and collections of structures that generally form the named shape.

FIGS. 2 and 4 illustrate how the exemplary well 106 may include a second well shape 207 to accommodate and hold the second vial 114. The second well shape 207 includes a second lateral support that retains the bottom end of the second vial 114 in the lateral direction, and a second vertical support that supports the second vial 114 in the vertical direction. In the exemplary embodiment, the second lateral support comprises a second cylindrical wall 208, and the second vertical support comprises a second radial wall 210. The second cylindrical and radial walls 208, 210 may be constructed like the first cylindrical and radial walls 202, 204 described above, and include features such as a taper or a separate flexible gripping device. A chamfer 212 or rounded lip may be provided at the top of the second cylindrical wall 208, joining it to the first radial wall 204, and facilitating insertion of the sample vial by increasing tolerance to misalignment.

FIGS. 2 and 5 illustrate a third well shape 213 to accommodate and hold the third vial 116. The third well shape 213 includes a third lateral support to hold the third vial 116 in the lateral direction, and a third vertical support to support the third vial 116 in the vertical direction. The exemplary third lateral support is shown as a third cylindrical wall 214, which may be a portion of the same wall that forms the second cylindrical wall 208. The exemplary third vertical support comprises a conical wall 216 that is positioned inward of and extends downward from the second radial wall 210. The conical wall 216 generally matches the conical bottom end of the third vial 116, and prevents it from moving downward. It will be appreciated that the conical wall 216 also may provide a degree of lateral support for the vial 116, and where the shape of the vial permits, a single conical wall may be used to provide all of the necessary vertical and lateral support. In addition, in other embodiments the conical wall 216 may be replaced by a radial wall or an other horizontal wall that supports only the tip of the contoured bottom end 116c of the third tube 116.

FIGS. 2 and 6 illustrate the manner in which the fourth vial 118 is held in the rack 100. In this embodiment, the bottom end 118c of the fourth vial 118 has approximately the same dimensions and shape as the bottom 114c of the second vial 114, and his held in the rack 100 in the same way.

It will be seen from the foregoing embodiments that a combination of well shapes can be provided to accommodate a variety of different sample tubes in a single rack well. Generally, the well has sufficient structures to hold each vial vertically and laterally. The shown structures extend downward from the upper surface 104 of the rack 104 in the order of: a first cylindrical wall 202 having a relatively large diameter, a first radial 204 wall extending inward from the first cylindrical wall 202, a second cylindrical wall 208 extending downward from the first radial wall 204, a second radial wall 210 extending inward from the second cylindrical wall 208, and a conical wall 216 extending downward from the second radial wall 210. The vertical positions of the first and second radial walls 204, 210 and the conical wall 216 may be selected, as explained in more detail below, to position the various vials at particular heights to facilitate processing. In addition, the well 106 may be configured to hold the wells substantially concentrically for reasons described below.

The foregoing exemplary sample rack 100 has been found to be beneficial from a manufacturing standpoint, in that wells having this construction are readily formed as a unitary part of a tray using simple injection molding techniques, but this aspect is not required of all embodiments. In other embodiments, other structures may be used to provide the necessary lateral and vertical support for the vials. For example, the cylindrical walls may be replaced by discrete ring shapes, by holes formed in vertically-spaced plates, by a series of vertically-extending pins that rise from a common bottom wall, or by other shapes. The arrangement also may be inverted so that the various walls extend upwards from a common bottom wall. Also, the number of vials being supported in the rack may be decreased to as few as two, or increased to as many as practical. Furthermore, it will be appreciated that, while each sample well in the shown rack may be adapted to hold multiple sample vial sizes, the rack may be modified so that some wells can hold only a single size vial. This may be desirable, for example, where samples of one size greatly outnumber samples of other sizes, leading to less need to use alternative sample sizes in each well, or where it is desired to locate vials containing control reagents in the racks.

As noted above, additional grips, spring-loaded tabs, or other devices may be provided to help hold different size vials. However, it is preferred to avoid the use of such devices. In a preferred exemplary embodiment, the wells 106 are formed simply from shaped material (and may include a friction-generating material such as an overmolded soft rubber), and can hold at least two different vials without needing moving parts or added clips, adapters or other devices that may complicate the design, reduce reliability or add to costs. While additional vials may be added to a well using such adapters or parts, it may be more preferable to avoid the use of such devices.

Referring to FIGS. 2-5, the wells 106 may be adapted to hold vials having various shapes such that the tops of the vials are in a predetermined location to be received by a gripper 220. As shown in FIG. 2, an exemplary gripper 220 comprises two opposed fingers, 222 that can be moved simultaneously towards and away from one another to grasp the vials. To help ensure that the vials are not excessively tipped by being contacted by one finger long before being contacted by the other finger, the vials preferably are held concentrically within the well. The gripper's movement may be linear and generally constrained to the horizontal plane, but other movement paths may be used instead.

Other embodiments may use other kinds of grippers, such as grippers having more than two fingers 222, fingers that move in rotary fashion, a combination of fixed and moving fingers, strap-type grippers, flexible bellows, and other mechanisms. As long as the gripper does not excessively tip or move the vial as it closes and engages the vial, any gripper type may be used. For example, a gripper using one or more fixed fingers and one or more movable fingers may be used, provided it does not excessively tip the vials during engagement. To this end, an embodiment using a gripper having fixed fingers may have rack wells that are modified to hold the different size vials non-concentrically, so that one side of each vial size is relatively close to the fixed finger during the engagement process and movement of the movable finger can not excessively tip a smaller-diameter vial by traveling a relatively large distance towards the fixed finger after contacting the vial.

The fingers 222 may be operated by any suitable motor, such as pneumatic or hydraulic piston or an electric motor, and may include any suitable linkage or actuation members to obtain the desired movement. The design and implementation of suitable gripper drives and linkages are well within the purview of the person of ordinary skill in the art and need not be described herein.

Each finger 222 may include one or more grip surfaces adapted to grasp one or more of the various different vials. For example, in the shown embodiment, the fingers 222 each have a first grip member 224 adapted to grasp a respective side of the first vial 112, and a second grip member 226 adapted to grasp a respective side of the second vial 114 or the third vial 116. The first and second grip members 224, 226 may be planar or have a curve that generally matches the outer circumference of the vials, and may include a rubber grip or other grip-enhancing features.

The first grip members 224 are located below and spaced further apart than the second grip members 226. As shown in FIGS. 3-5, the well 106 is configured such that the gripper 220 can be lowered to a predetermined height $H_1$ away from the rack 100, at which height the first grip members 224 are positioned to grasp the top of the first vial 112. At this same height $H_1$, the second grip members 226 are positioned to grasp the tops of the second and third vials 114, 116. Thus, the gripper 220 need only be lowered to a single predetermined height $H_1$ in order to pick up the first, second or third vials 112, 114, 116, despite significant differences in the shapes of these vials. As shown in FIG. 6, the fourth vial 118 may be significantly shorter than the other vials, and it may be necessary to lower the gripper 220 to a lower second height $H_2$ to pick up the fourth vial 118 using the second grip members 226.

In an alternative embodiment, one of the grip members 224,226 may be omitted, and the well 106 may be adapted to hold the vials 112, 114, 116 such that their tops are all at the same height where they can be grasped by as single grip member. However, given the large difference in diameter between these vials and the added design complexity that may arise from providing a single set of grip members having sufficient range of motion to grasp both large and small vials, it has been found that using a single gripper with multiple grip members is a suitable and useful design option.

Racks 100 according to exemplary embodiments, may be used much like a conventional rack that holds only one kind of sample container. The operator may load the rack 100 with samples provided in a variety of different sample containers, such as the shown vials 112, 114, 116, 118. The rack 100 preferably can be inserted into a system, such as the pre-analytic system described in U.S. application Ser. No. 12/588,304 (previously incorporated herein), which can use a gripper, such as gripper 220, to selectively remove each sample vial from the rack 100 for processing, then return the sample vial to the rack. Before installing the rack, the user may program the system to identify the type of vial held in each well. Alternatively, the system may include scanners that determine the types of vials as or after they are loaded into the system. For example, a barcode scanner may scan each vial to identify a vial type associated with the barcode, or a shape detection system may be used to visually inspect and identify each vial. In a more preferred system, however, the system can pick up the vials from the rack without being informed what kind of vial is at each rack location. In such an embodiment, the vial pickup system also may identify the type of vial as it picks it up from the rack, or the type of vial may be determined at a downstream processing location, such as at a barcode scanning location associated with the gripper or with another processing station. Regardless of how the vial type is identified, the system may store that vial type in a map that is used, where necessary, to perform any processing steps unique to samples contained in each kind of vial. For example, where two different kinds of vial contain different amounts or kinds of sample storage media, it may be necessary to process samples taken from those samples differently. By mapping the kind of vial—and thus the kind of sample presumably contained in the vial—the system can track the sample extracted from that vial and perform the proper processing steps for that sample type as it progresses through any number of processing steps.

Figure 7:
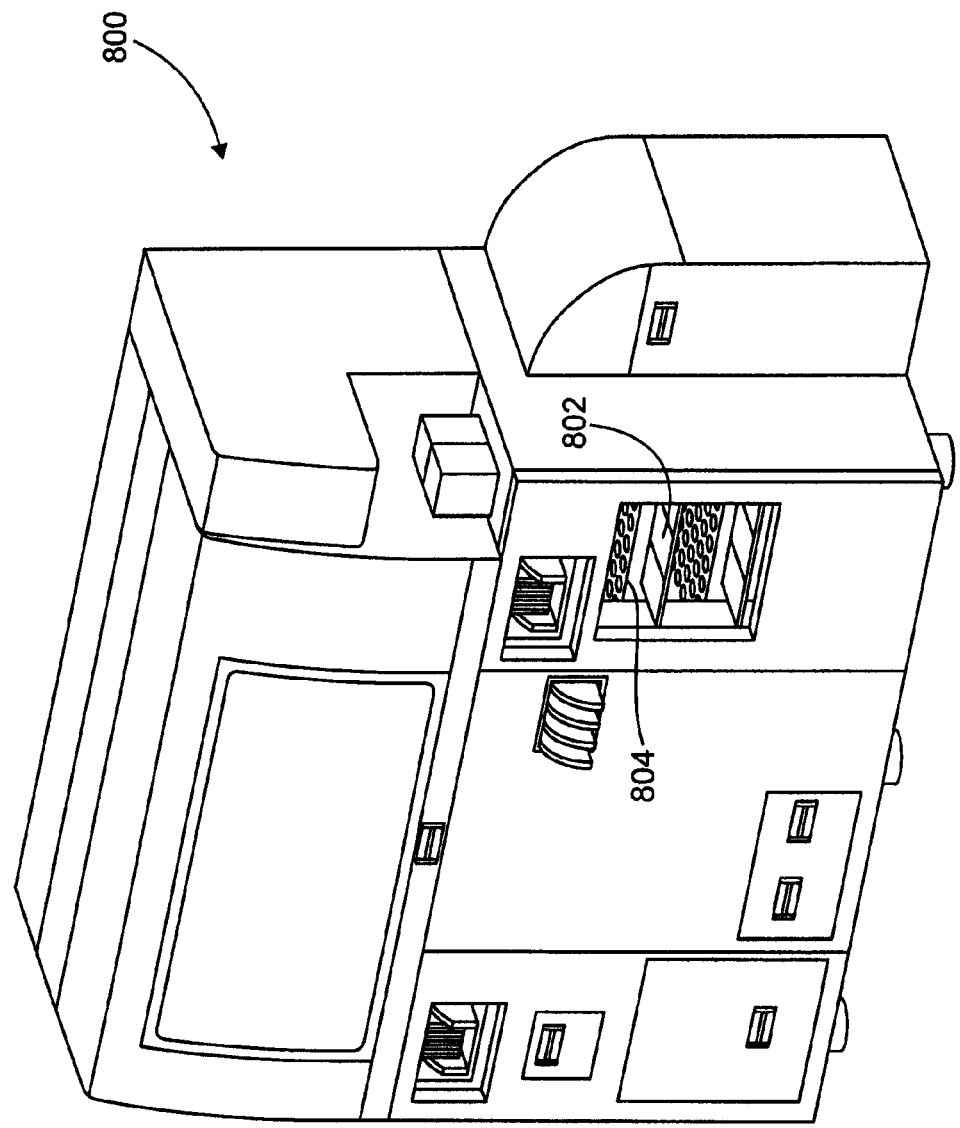
FIG. 7 is an isometric view of an exemplary pre-analytic automated sample processing system.
Figure 8:
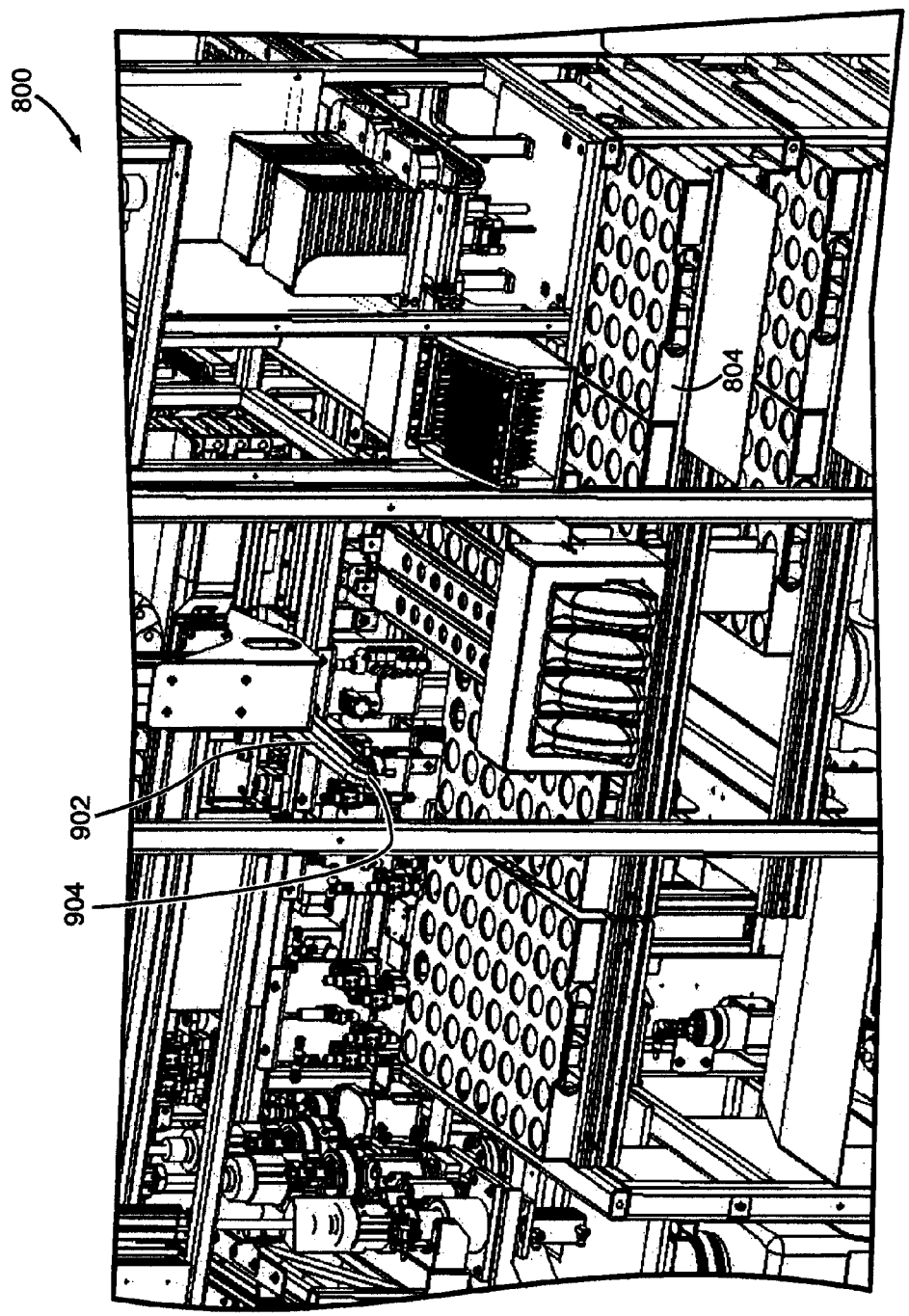
FIG. 8 is a partial view of the automated sample processing system of FIG. 7, shown with a front panel removed to see an exemplary access arm and gripper.

FIGS. 7 and 8 show an exemplary pre-analytic automated sample processing system ("PAS") 800 that may be used with the present invention. As shown in FIG. 7, the PAS 800 includes one or more inlets 802 to receive sample racks 804. As shown in FIG. 8, the PAS 800 may include an access arm 902 that mounted to move in various directions, such as pivotally, vertically and/or laterally, within the PAS 800. The access arm 902 has a gripper 904, such as described herein.

Referring to FIGS. 2-5, the rack 100 and gripper 220 may be configured and operated so that an automated system pick up any of a number of different kinds of vial without being pre-notified of the vial type. As noted above, the shown vials 112, 114, 116 are all positioned at an appropriate height where the staggered grip members 224, 226 can grasp any kind of vial. In operation, the system positions the gripper 220 a predetermined distance $H_1$ above a well 106, with the fingers 222 spread apart wide enough to clear any expected vial size. The gripper 220 may be placed in this starting position by moving it vertically downward towards the rack 100, moving it laterally (where the fingers spread wide enough to clear the tops of the vials), or by a combination of movements. The rack 100 may be held still during the positioning process, or it may be moved along with or instead of the gripper 220.

Once in position at the predetermined height $H_1$, the gripper closes the fingers 222 towards each other until the first or second grip members 224, 226 contact and grasp a vial. For example, if a first vial 112 is in the well 106, the fingers 222 will close a relatively short distance before the first grip members 224 engage the first vial 112, as indicated by the remaining gap $W_1$ between the fingers 222. If a second vial 114 is in the well 106, the fingers 222 will close until the second grip members 226 engage the vial lid 114b, which surrounds and has a slightly larger diameter than the vial body 114a, leaving a smaller gap $W_2$ between the fingers 222. Similarly, if a third vial 116 is in the well 106, the fingers 222 will close on the third vial body 116a, due to the lid 116b being internal, rather than external, to the body 116a, and leave an even smaller gap $W_3$ when the second grip members 226 engage the vial. In this embodiment, it is unnecessary for the gripper 220 to move vertically to engage any of the three vial types, which simplifies the programming and may permit the use of relatively simple and less expensive processing equipment. Nevertheless, in other embodiments some vertical movement may be provided in the gripper's closing path.

Once the gripper 220 properly engages a vial, further closing of the fingers 222 may be prevented by any suitable overload prevention system. For example, the total available closure force may be limited to a level that permits suitable grasping to lift and move the vials, but prevents distortion or damage to the vials (e.g., by using an overload clutch in the closure mechanism, using low-force pneumatic drives, etc.), or the closure force may be limited by a control circuit (e.g., sensing closure pressure with a pressure sensor, limiting closure distance based on an optical measurement of vial size, using force feedback motor controls, etc.). Where a pushcap is used to seal the top of the vial, such as cap 116b used on vial 116, the gripper 220 may be shaped or engaged with sufficient closing pressure to the vial wall that the gripper 220 does not remove the cap 116b and leave the vial 116 in the rack 100.

The gripper 220 also may include features to identify the type of vial. For example, an encoder may be positioned on one or both fingers 222 or on a force-feedback motor system to measure the location at which the gripper 220 engaged the vial. The system can compare this measurement with a table of known vial diameters (which may account for known or measured vial size variations and encoder error ranges) to determine the type of vial being grasped in the gripper 220. In other embodiments, one or more optical sensors may be provided to determine the vial type being addressed. For example, a first optical sensor 228 may be positioned above one of the first grip members 224 to detect when a vial of the first type 112 is present in the first grip members 224. The presence of the second or third vial 114, 116 may be determined using similar optical sensors. For example, a pair of sensors comprising a second optical sensor 230 located directly above the second grip member 226 and a third optical sensor 232 located above the second grip member, but radially inward from the second optical sensor 230, may be provided. When the second vial 114 is present, both sensors will indicate the presence of an object, but when the third vial 116 is present, the second sensor 230 will detect an object, but the third sensor 232 will not detect an object due to the presence of a bore 502 (FIG. 5) in the center of the third vial cap 116b. Optical sensors such as these also can be used to detect whether no tube is present at the well, or monitor the presence of the tube in the gripper during transport and indicate an error condition if the tube should fall out of the gripper.

After the gripper 220 engages the vial, it lifts it out of the well 106, and conveys it for further processing. During such processing, if the vial identity is not yet determined, the system may scan an identifier on the vial, such as a barcode or a radio-frequency identification signal, to identify the vial and sample type, and use this information in later processing steps. For example, the gripper may pass the sample vial past a barcode scanner as it conveys it to a decapping, pipetting, and capping system where the lid is removed, a sample is removed, the lid is replaced, and the sample is presented to the gripper to return it to the tube's original location on the rack.

Referring to FIG. 6, in some cases a sample vial 118 may be shaped or dimensioned such that a gripper 220 operating at a predetermined height $H_1$ for other vials will not be properly positioned to engage the vial 118. In such cases, the gripper 220 may be operated according to a more elaborate movement path to engage such vials. In the shown embodiment, for example, the vial 118 is appropriately sized to be gripped in the second grip members 226, but is too short to be engaged as the gripper 220 moves at the first height $H_1$. In this embodiment, the gripper 220 is programmed to close horizontally at the first height $H_1$, and if no vial is detected or picked up at that level, to open slightly, move to a lower height $H_2$, and begin closing again. If vial 118 is found at the second height $H_2$, the vial is removed for further processing. Controller logic, such as a register entry indicating that the gripper 220 was lowered before engaging the vial 118, may be used to map the vial as being the shorter type, and this information may be used to control the gripper 220 and lower it further when the vial 118 is being returned to the well 106. Where none of the vials in a given rack (or none used in a processing system) require operating the gripper 220 at a separate height, it may not be necessary to take into account the vial type when the gripper returns each vial to the rack, as the vertical travel to return each vial to the rack 100 will be the same.

EXAMPLE

The illustrated exemplary embodiment is designed to hold forty-eight (48) samples vials having various shapes and sizes. Some or all of the sample vials may be used as collection vials for cytology samples taken from a human cervix, and intended to be tested for the presence of human papilloma virus ("HPV") DNA or other viruses or conditions. The first vial 112 comprises a "PreservCyt" vial provided by Qiagen. The second vial 114 comprises a 10 milliliter ("ml") Sarstaedt round tube with a flat skirt. The third vial 116 comprises a 12 ml Sarstaedt conical tube. The fourth vial 118 comprises another Qiagen vial. Any mixture of these tube types may be held in the rack 100, and the rack 100 may be used to store the vials, or transport the vials from lab to lab, such as between cytology and HPV testing labs. The rack 100 also may be configured for use as a sample rack in a pre-analytic system, such as the one described in U.S. application Ser. No. 12/588,304 (previously incorporated herein), and shown in FIGS. 2 and 4 thereof.

It also will be appreciated that embodiments of the invention may be used in any number of clinical sample testing applications and in any number of testing, analysis or pre-analysis equipment or machines. For example, racks and grippers according to the invention may be used in an automated processing system used to perform steps required in many common clinical or research laboratory methods. Exemplary embodiments can be used with a DNA analysis assay, such as Qiagen's Next Generation Hybrid Capture® High Risk and Hybrid Capture 2 assays. Other assays include those disclosed in U.S. Provisional Application Ser. No. 61/231,371, filed Aug. 5, 2009, entitled "METHODS AND KITS FOR ISOLATING NUCLEIC ACIDS USING AN ANION EXCHANGE MATRIX" and Ser. No. 61/147,862, filed Jan. 28, 2009, entitled "SEQUENCE SPECIFIC LARGE VOLUME SAMPLE PREP SOLUTION UTILIZING HYBRID CAPTURE TECHNOLOGY," which are incorporated herein by reference in their entireties. In other embodiments, the invention may be applied to other assays or clinical processes directed towards other clinical tests.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A rack for an automated processing system, the rack comprising:
   a plurality of wells, each of the plurality of wells being adapted to selectively hold at least a first sample container having a first size and a second sample container having a second size, the second size being substantially different from the first size; and a structure joining the plurality of wells to form a rack;

wherein the rack is adapted to fit in an automated processing system adapted to remove both the first sample container and the second sample container from the rack;

wherein each of the plurality of wells is further adapted to hold a third sample container having a third size, the third size being substantially different from at least one of the first size and the second size; and wherein each of the plurality of wells comprises:
  a first cylindrical wall;
  a first radial wall below the first cylindrical wall and extending inward from the first cylindrical wall;
  a second cylindrical wall extending below the first radial wall;
  a second radial wall below the second cylindrical wall and extending inward from the second cylindrical wall;
  a conical wall extending below the second radial wall.

2. The rack of claim 1, wherein each of the plurality of wells comprises:
  a first well shape having a first lateral support to hold the first sample container in a lateral direction, and a first vertical support to support the first sample container in a vertical direction; and
  a second well shape having a second lateral support to hold the second sample container in the lateral direction, and a second vertical support to support the second sample container in the vertical direction.

3. The rack of claim 2, wherein at least one of the first well shape and the second well shape comprises a cylindrical wall and a radial wall extending from the bottom of the cylindrical wall.

4. The rack of claim 2, wherein at least one of the first well shape and the second well shape comprises a conical wall adapted to contact a portion of at least one of the first sample container and the second sample container.

5. The rack of claim 4, wherein at least one of the first well shape and the second well shape further comprises a cylindrical wall above the conical wall.

6. An automated sample processing system comprising:
  a first sample container;
  a second sample container having at least one dimension that is substantially different from at least one corresponding dimension of the first sample container;
  a rack having a plurality of wells, each of the plurality of wells being configured to alternately hold the first sample container and second sample container, and a structure joining the plurality of wells;
  a processing machine adapted to receive the rack, the processing machine having a gripper having one or more movable grips adapted to alternately grasp the first sample container and the second sample container to permit the gripper to remove the first sample container and the second sample container from the rack;
  wherein the processing machine comprises a pre-analytic machine adapted to perform a first plurality of assay steps on first samples removed from the first container and a second plurality of assay steps on second samples removed from the second container, wherein at least one of the first plurality of assay steps is different from at least one of the second plurality of assay steps.

7. The automated sample processing system of claim 6, wherein the at least one dimension comprises a second sample container diameter, and the at least one corresponding dimension comprises a first sample container diameter.

8. The automated sample processing system of claim 6, wherein the at least one dimension comprises a second sample container height, and the at least one corresponding dimension comprises a first sample container height.

9. The automated sample processing system of claim 6, wherein the at least one dimension comprises a second sample container diameter and a second sample container height, and the at least one corresponding dimension comprises a first sample container diameter and a first sample container height.

10. The automated sample processing system of claim 6, wherein the rack is removable from the processing machine.

11. The automated sample processing system of claim 6, wherein the one or more movable grips each comprise two grips, each grip having a first grip member and a second grip member, and wherein the first grip members are below the second grip members and spaced a greater distance from one another than the second grip members at any given position of the movable grips.

12. The automated sample processing system of claim 6, wherein the gripper comprises one or more sensors positioned to detect the presence of the first sample container or the second sample container.

13. The automated sample processing system of claim 12, wherein the one or more sensors identify one or more distinctions between the first sample container and the second sample container.

14. The automated sample processing system of claim 6, wherein the one or more movable grips have a movement path between an open position and a closed position, the movement path extending generally in a horizontal plane.

15. The automated sample processing system of claim 14, wherein the plurality of wells are adapted to hold the first sample container with an upper end of the first sample container at a first height, and to hold the second sample container with an upper end of the second sample container at a second height, wherein the first height and the second height are within the movement path.

16. The automated sample processing system of claim 15, wherein the one or more movable grips comprise at least two lower grip members and at least two upper grip members, wherein the lower grip members are spaced a greater distance from one another with respect to the horizontal plane than the upper grip members, and wherein the lower grip members are located in a lower portion of the movement path, and the upper grip members are located in an upper portion of the movement path.

17. The automated sample processing system of claim 15, wherein the upper end of the first sample container is positioned to be grasped by the lower grip members, and the upper end of the second sample container is positioned to be grasped by the upper grip members.

18. The automated sample processing system of claim 6, further comprising:
  a third sample container having at least one third dimension that is substantially different from at least one corresponding dimension of the first sample container and the second sample container;
  wherein each of the plurality of wells is adapted to alternately hold the first sample container, the second sample container and the third sample container; and
  wherein the movable grips are adapted to alternately grasp the first sample container, the second sample container and the third sample container to permit the gripper to remove the first sample container, the second sample container and the third sample container from the rack.

19. A rack and sample container system comprising:
a first sample container having a first height;
a second sample container having at second height;
a third sample container having a third height; and
a rack having a plurality of wells, each of the plurality of wells comprising:
- a first well shape adapted to hold the first sample container with an upper end of the first sample container at a first predetermined distance from the rack,
- a second well shape adapted to hold the second sample container with an upper end of the second sample container at a second predetermined distance from the rack, and
- a third well shape adapted to hold the third sample container with an upper end of the third sample container at a third predetermined distance from the rack;
wherein the first predetermined distance, second predetermined distance and third predetermined distance are approximately the same distance from the rack, such that the upper end of the first sample container, the upper end of the second sample container, and the upper end of the third sample container are within a generally linear travel path of an associated gripping mechanism.

20. The rack and sample container system of claim 19, wherein at least two of the first well shape, the second well shape and the third well shape comprise common structural elements.

21. The rack and sample container system of claim 19, wherein:
the first well shape comprises a first cylindrical wall and a first radial wall below the first cylindrical wall and extending inward from the first cylindrical wall;
the second well shape comprises a second cylindrical wall extending below the first radial wall and a second radial wall below the second cylindrical wall and extending inward from the second cylindrical wall; and
the third well shape comprises at least a portion of the second cylindrical wall and a conical wall extending below the second radial wall.

22. The rack and sample container system of claim 19, wherein the first well shape, second well shape and third well shape are concentrically arranged.

* * * * *